United States Patent [19]

Kirchner

[11] Patent Number: 5,481,027

[45] Date of Patent: Jan. 2, 1996

[54] FLUOROCARBAMATE SOIL-RELEASE AGENTS

[75] Inventor: Jack R. Kirchner, Wilmington, Del.

[73] Assignee: E. I. Du Pont de Nemours and Company, Wilmington, Del.

[21] Appl. No.: 207,527

[22] Filed: Mar. 7, 1994

Related U.S. Application Data

[63] Continuation-in-part of Ser. No. 843,708, Feb. 28, 1992, abandoned, and a continuation-in-part of Ser. No. 190,704, Feb. 21, 1994, Pat. No. 5,414,111, which is a continuation of Ser. No. 34,628, Mar. 22, 1993, abandoned, which is a continuation of Ser. No. 790,097, Nov. 6, 1991, abandoned, which is a continuation-in-part of Ser. No. 459,060, Dec. 29, 1989, abandoned.

[51] Int. Cl.$^6$ ............... C07C 267/00; C07C 265/02; D06M 15/576

[52] U.S. Cl. ............... 560/160; 560/158; 560/337; 560/357; 560/358; 252/8.8; 252/8.9

[58] Field of Search ............... 560/158, 160, 560/337, 357, 358; 252/8.6, 8.8, 8.9

[56] References Cited

U.S. PATENT DOCUMENTS

| | | | |
|---|---|---|---|
| 4,668,406 | 5/1987 | Chang | 252/8.75 |
| 4,689,353 | 8/1987 | Harris | 521/159 |
| 4,748,267 | 5/1988 | Chang | 560/158 |
| 4,788,287 | 11/1988 | Matsuo et al. | 544/196 |
| 4,877,540 | 10/1989 | Engelhardt et al. | 252/8.75 |
| 5,015,753 | 5/1991 | Harris | 558/260 |
| 5,410,073 | 4/1995 | Kirchner | 560/357 |
| 5,411,766 | 5/1995 | Kirchner | 252/8.75 |
| 5,414,111 | 5/1995 | Kirchner | 560/357 |

FOREIGN PATENT DOCUMENTS

| | | | |
|---|---|---|---|
| 0172717 | 2/1986 | European Pat. Off. | 560/158 |
| 0304016 | 2/1989 | European Pat. Off. | 560/158 |

*Primary Examiner*—Shean Wu

[57] ABSTRACT

Urea linkage-containing alkoxypolyoxyalkylene fluorocarbamates prepared by reacting (a) at least one polyisocyanate which contains at least three isocyanate groups with (b) at least one fluorochemical reagent which contains one functional group which has at least one H and at least two C atoms each of which contains at least two F atoms, (c) at least one hydrophilic, water-solvatable reagent which contains a single functional group which has at least one reactive H, (d) at least one reagent which contains one reactive H and which on reaction with an isocyanate group yields functionality which has abeyant chemical reactivity with fibrous substrates and (e) then with water, reactants (b), (c) and (d) being reacted with 55% to 95% of said isocyanate groups, and water with the remainder.

9 Claims, No Drawings

FLUOROCARBAMATE SOIL-RELEASE AGENTS

CROSS-REFERENCE TO RELATED APPLICATIONS

This is a Continuation-in-Part of application Ser. No. 07/843,708 filed Feb. 28, 1992. It is also a Continuation-in-Part of application Ser. No. 08/190,704 filed Feb. 21, 1994, which in turn is a Continuation of application Ser. No. 08/034,628 filed Mar. 22, 1993, which in turn is a Continuation of application Ser. No. 07/790,097 filed Nov. 6, 1991, which in turn is a Continuation-in-Part of application Ser. No. 07/459,060 filed Dec. 29, 1989. All of the foregoing applications are now abandoned except for application Ser. No. 08/190,704 filed Feb. 21, 1994, now U.S. Pat. No. 5,414,111.

FIELD OF THE INVENTION

The present invention relates to novel, fiber-reactive urea linkage-containing alkoxypolyoxyalkylene fluorocarbamates and their use to provide durable oil-repellency, durable soil-repellency and durable soil-release properties to textiles, and to novel processes for preparing the fiber-reactive fluorocarbamates.

BACKGROUND OF THE INVENTION

The treatment or modification of fabrics to improve their properties is routine practice in the textile industry. For instance, thermosetting organic resins are often used to impart "wash and wear" or "permanent press" characteristics to such fabrics as cotton, cotton polyester blends and other cellulosic blends which naturally wrinkle badly when cleaned or laundered. Various modifying additives or finishing agents such as softeners, stiffeners, lubricants, etc., are also commonly employed with the resin to provide a suitable commercial fabric. These treatments/modifications typically increase the oleophilicity of the fabric, thereby significantly increasing its tendency to accept oily stains and reducing its ability to release such stains after laundering.

The resin treated/modified fabrics can be co-treated with hydrophilic materials to reduce their oleophilicity and facilitate stain release during laundering. These materials, which are referred to as soil release agents, can be hydrophilic colloids such as carboxymethylcellulose, synthetic hydrophilic polymers such as polyacrylic acid, or fluorochemical-based systems. The latter, which may comprise physical mixtures of a fluorinated oil/water repellent and a non-fluorinated hydrophilic derivative or chemical hybrids containing both fluorinated oleophobic and non-fluorinated hydrophilic segments, are particularly advantageous, since they provide oil repellency during normal wear and inhibit "wicking" or diffusion of oily soils into the fabric or fiber bundles, as well as facilitate soil release during laundering.

The prior art fluorinated soil release products typically have one or more of the following disadvantages:

They are prepared by multi-step, less-than-quantitative yield procedures which require the isolation and purification of one or more intermediate reaction products, and/or are utilized as solutions in organic solvents which are toxic, flammable and/or expensive or as surfactant stabilized emulsions or dispersions which tend not to be freeze/thaw or shear stable, or which have poor compatibility and stability with textile mill finish baths and/or are not overly wash durable when applied to textile fabrics.

The products of the present invention, in contrast, provide mobile, "high" solids content, organic solvent-free, surfactant-free, freeze/thaw-stable, shear-stable, aqueous systems which (a) are compatible with and stable in commercial textile fabric finish formulations, (b) impart enhanced and wash durable soil release properties to fiber containing fabrics and (c) are readily prepared from commercially available raw materials by a simple, high yield process.

SUMMARY OF THE INVENTION

The fluorochemical products of the present invention comprise compounds which are prepared by the reaction of (1) at least one polyisocyanate which contains at least three isocyanate (NCO) groups per molecule with (2) at least one fluorochemical reagent which contains per molecule a single functional group which has at least one reactive hydrogen atom as defined by Zerevitinov in Berichte, 40,2023 (1907) and at least two carbon atoms each of which contains at least two fluorine atoms, (3) at least one hydrophilic, water-solvatable reagent which contains per molecule a single functional group having at least one Zerewitinoff reactive hydrogen atom as defined above, (4) at least one reagent which contains at least one Zerewitinoff reactive hydrogen atom and which, on reaction with an NCO group, yields functionality having abeyant chemical reactivity with fibrous substrates which contain reactive Zerewitinoff hydrogen atoms, and (5) then with water. The reaction is carried out in an organic solvent which is chemically inert to the reactant charge and which is subsequently removed and replaced by water to obtain the fluorochemical compound or mixture thereof as a mobile, organic solvent-free, and surfactant-free, freeze/thaw and shear-stable aqueous dispersion. When the fibrous substrate contains cotton or nylon or the like, the fibrous substrate will itself provide said reactive hydrogen atoms. When used on fibrous substrates which do not themselves contain such reactive hydrogens, the urea linkage-containing polyoxyalkylene fluorocarbamates of this invention may none-the-less be reactive with the fibrous substrate because of its content of textile adjuvants which contain such reactive hydrogen atoms. When co-applied to fabrics with other textile adjuvants which otherwise increase the tendency of the fabric to accept and retain oily soils, i.e., with agents used to enhance the "hand", crease resistance or processability of the fabric, the fluorochemical compounds provide (A) a durable, oleophobic and hydrophobic dry fabric surface coating which repels oily soils from and inhibits their spread and/or "wicking" into the fabric or fiber bundles and (B) a hydrophilic fabric surface coating during laundering which facilitates the removal of oily soils by permitting water and detergent to diffuse to the oil/fiber interface.

DETAILED DESCRIPTION OF THE INVENTION

Any polyisocyanate, or mixture thereof, having three or more isocyanate groups can be used for the purposes of this invention. For example, one can use hexamethylene diisocyanate homopolymers having the formula:

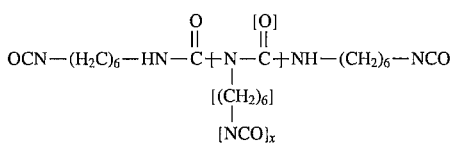

wherein x is an integer equal to or greater than 1, preferably between 1 and 8. Because of their commercial availability, mixtures of such hexamethylene diisocyanate homopolymers are preferred for purposes of this invention. Also of interest are hydrocarbon diisocyanate-derived isocyanurate trimers which can be represented by the formula:

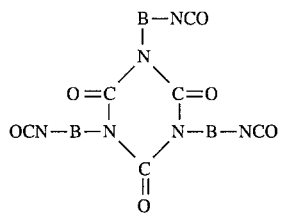

wherein B is a divalent hydrocarbon group, preferably aliphatic, alicyclic, aromatic or arylaliphatic. For example, B can be hexamethylene (Desmodur N-3300, Mobay Corporation), toluene or cyclohexylene (Polyisocyanate IPDI Adduct T 1890/100, Huls). Other polyisocyanates useful for the purposes of this invention are those of the following general formula:

$$\begin{array}{c} CH_2-OCONHR^{14} \\ | \\ R^{13}-C-CH2OCONHR^{14} \\ | \\ CH_2OCONHR^{14} \end{array}$$

in which $R^{13}$ is a methyl or ethyl radical and $R^{14}$ is

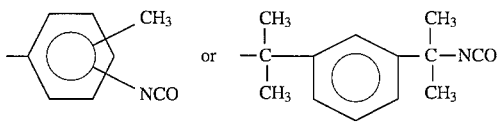

Also useful for the purposes of this invention is 1,6,11-undecane triisocyanate,

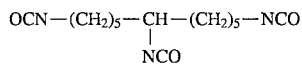

as is methine-tris(phenylisocyanate) and the polyisocyanate having the formula:

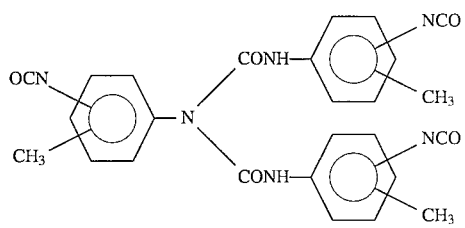

The oleophobic/hydrophobic properties of the fluorochemical compounds of the present invention are derived from their fluorochemical components (2). A wide variety of fluorochemical reagents, or mixtures thereof, can be used for the fluorochemical component so long as each contains a single functional group having one or more reactive hydrogen atoms as defined above and at least two carbon atoms each of which contains at least two fluorine atoms. It is advantageous for the fluorochemical reagent, or mixture thereof, to contain more than two fluorine saturated carbon atoms, however, since the fluorine content of the final product is in part dependent on the fluorine content of the fluorochemical reagent per se and on the number of fluorochemical moieties incorporated therein. It is desirable, but not essential that the final product contain >10% by weight fluorine (100% basis).

Unless otherwise noted, the fluorochemical reagent (2) used in the Examples is a perfluoroalkylethyl alcohol mixture (FA) of the formula $F(CF_2)_aCH_2CH_2OH$, wherein a is predominantly 6,8 and 10. In a typical mixture of such fluoroalcohols, the compounds will have the following approximate composition in relation to their $F(CF_2)_a$ radicals:

0% to 3% wherein a=4,
27% to 37% wherein a=6,
28% to 32% wherein a=8,
14% to 20% wherein a=10,
8% to 13% wherein a=12,
3% to 6% wherein a=14,
0% to 2% wherein a=16,
0% to 1% wherein a=18, and
0% to 1% wherein a=20

Other fluorochemical reagents which can be used and for which examples are provided include:

A perfluoroalkylethyl alcohol mixture (FNA) of the formula shown above wherein a is predominantly 8, 10 and 12. In a typical mixture of such fluoroalcohols, the compounds will have the following approximate composition in relation to their $F(CF_2)_a$ radicals:

0% to 3% wherein a=6,
45% to 52% wherein a=8,
26% to 32% wherein a=10,
10% to 14% wherein a=12,
2% to 5% wherein a=14,
0% to 2% wherein a=16,
0% to 1% wherein a=18, and
0% to 1% wherein a=20

A perfluoroalkylethyl thiol mixture of the formula $F(CF_2)_aCH_2CH_2SH$, wherein a is predominantly 8, 10 and 12. In a typical mixture of such fluorothiols, the compounds will have the approximate composition in relation to their $F(CF_2)_a$ radicals as shown above for the FNA fluoroalcohol mixture.

A perfluoroalkylpropyl amine mixture of the formula $F(CF_2)_aCH_2CH_2CH_2NH_2$ wherein a is predominantly 8, 10 and 12. In a typical mixture, the fluoroalkylpropyl amines will have the approximate composition in relation to their $F(CF_2)_a$ radicals as given above for the thiol mixture.

A perfluoroalkylmethyl alcohol of the formula $F(CF_2)_aCH_2OH$ wherein a is 5.

A N-alkyl-N-ethanolperfluoroalkylsulfonamide of the formula $F(CF_2)_aSO_2N(R)CH_2CH_2OH$ wherein R is methyl or propyl and a is 8.

Hexafluoroisopropanol

A N-perfluoroalkylethyl-N-phenylamine mixture of the formula $F(CF_2)_aCH_2CH_2—NH—C_6H_5$, wherein a is predominantly 6 and 8.

A mixture of diperfluorooctylethylamine and N-perfluoro-octylethyl-N- 3,4,4,5,5,6,6,7,7,8,8,9,9-10,10,10-hexadecafluoro-2-decene-1-amine.

The soil-release properties and the mobility, solids content, freeze/thaw, shear, and aqueous dispersion stability attributes of the fluorochemical compounds of the present invention are derived from the hydrophilic, water-solvatable component (3). A large number and variety of hydrophilic, water-solvatable materials can be used to obtain soil release properties in the fluorochemical products of this invention. However, in order to prepare the fluorochemical compounds of the present invention, it is essential that the water-solvatable, hydrophilic materials contain per molecule a single functional group having at least one Zerewitinoff active hydrogen atom. The resulting fluorochemical products are mobile, high solids content, freeze/thaw and shear-stable, surfactant- free aqueous dispersions that are compatible with commercial cellulosic fabric finish bath formulations. At the same time, they provide oil- and soil-repellency and durable soil-release properties to cellulosic fabrics and yield flurochemical products having a cloud point of 20° C. or higher (the temperature above which the products of this invention will not remain self-dispersed in water or aqueous commercial textile fabric finish formulations).

In a preferred embodiment, the hydrophilic water-solvatable component (3) is at least one ethylene oxide (EO) or ethylene oxide/propylene oxide (PO) derived polymer of the general formula

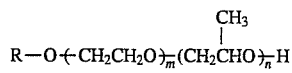

wherein R is a monovalent hydrocarbon radical containing no more than six aliphatic or alicyclic carbon atoms; m and n are the average number of repeating oxyethylene (EO) and oxypropylene (PO) groups, respectively; provided that m is always a positive integer, while n is a positive integer or zero (designating an EO homopolymer in the latter case).

More preferably, the hydrophilic, water-solvatable components (3) are the commercially available methoxypolyethylene glycols (MPEG's), or mixtures thereof, having an average molecular weight equal to or greater than about 350, and most preferably between 400 and 800. Also commercially available and suitable for the preparation of the polyfluoro organic compounds of the present invention are butoxypolyoxyalkylenes containing equal amounts by weight of oxyethylene and oxypropylene groups (Union Carbide Corp. 50-HB Series UCON Fluids and Lubricants) and having an average molecular weight greater than about 1000.

The soil-repellency and soil-release properties imparted to treated fibers or fabrics by the fluorochemical products of the present invention are retained in large measure after repeated laundering. The wash-durability property of the fluorochemical products is derived in part from that fraction of the NCO group functionality that has been converted by one or more reagent (4) to functionality having abeyant chemical reactivity and which subsequently reacts with the substrate under curing conditions. Reagents (4) which can be used to convert NCO groups into derivatives that show abeyant chemical reactivity include (A) NCO blocking agents (reagents which, when reacted with an isocyanate, will prevent its reaction at room temperature with materials that conventionally react with isocyanates but will permit that reaction to occur at a higher temperature) and (B) epoxyalcohols, such as 2,3-epoxy-1-propanol (glycidol).

Isocyanate blocking agent 4(A) can be any one of the those normally used to block isocyanates in urethane technology provided it (i) satisfies the property/process requirements for incorporation into the fluorochemical products of the present invention and (ii) yields a storage-stable product having an effective substrate reaction rate at commercial textile mill time, temperature and application parameters. For example, for the purposes of this invention, one can use ketoximes such as 2-butanone oxime, acetone oxime or cyclohexanone oxime; aryl alcohols such as phenol, cresol, o- or p-nitrophenol, o- or p-chlorophenol, naphthol, or 4-hydroxy-biphenyl; aryl mercaptans such as thiophenol; low pKa alcohols such as 2,2,2-trichloroethanol or 1,1,1,3, 3,3-hexafluoro-2-propanol; other active hydrogen-containing compounds such as diethyl malonate, acetyl acetone, ethyl acetoacetate, ethyl cyanoacetate or caprolactam; or inorganic compounds such as sodium bisulfite or hydroxylamine. 2-butanone oxime is the preferred reagent (4).

The reaction of water (5) with the residual NCO groups effectively increases the average molecular weight of the derived product mixture and the probability that each product moiety will have fluorochemical, hydrophilic/water-solvatable and abeyant chemical reactivity functionality.

The fluorochemical products of the present invention are prepared by reacting: (1) at least one polyisocyanate or mixture of polyisocyanates which contains at least three NCO groups per molecule with a stoichiometric deficiency of (2) at least one fluorochemical compound which contains per molecule (a) a single functional group having one or more reactive Zerewitinoff hydrogen atoms and (b) at least two carbon atoms each of which contains at least two fluorine atoms, (3) at least one hydrophilic, water-solvatable compound which contains per molecule a single functional group having at least one reactive Zerewitinoff hydrogen atom, and (4) at least one compound which contains at least one reactive Zerewitinoff hydrogen atom and which, on reaction with an NCO group, yields functionality having abeyant chemical reactivity with fibrous substrates which contain Zerewitinoff reactive hydrogen atoms. Thereafter the remaining NCO groups are then (5) reacted with water.

In order to achieve the advantageous properties set forth above, it is essential that each of elements (1) through (5), inclusive, be used to prepare the alkoxy polyoxyalkylene fluorocarbamates of this invention, and that those elements be present in the percentages described below. Thus, it is necessary that between about 7% and about 24% of the NCO groups will have been reacted with the fluorochemical compound, between about 8% and about 37% of the NCO groups will have been reacted with the hydrophilic, water-solvatable compound, and between about 15% and about 60% of the NCO groups will have been reacted with the compound imparting abeyant chemical reactivity to the product before the remaining NCO groups are reacted with water to form one or more urea linkages. Usually between about 55% and about 95% of the NCO groups will have been reacted before water is reacted with the polyisocyanate, preferably 65% to 80%. In other words, the amount of water generally is sufficient to react with from about 5% to about 45% of the NCO groups in the polyisocyanate, preferably 20% to 35%.

In one embodiment, fluorochemical products of the present invention have been prepared by the sequential catalyzed reaction of Desmodur N-100, Desmodur N-3200 or Desmodur N-3300, or mixtures thereof, with a stoichiometric deficiency of a perfluoroalkyl compound containing one functional group, a methoxypolyethylene glycol, a ketoxime, and then with water. Desmodur N-100 and Desmodur N-3200 are hexamethylene diisocyanate homopolymers commercially available from Mobay Corporation. Both presumably are prepared by the process described in U.S. Pat. No. 3,124,605 and presumably to give mixtures of the mono, bis, tris, tetra and higher order derivatives which can be represented by the general formula:

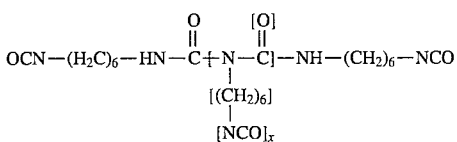

wherein x is an integer equal to or greater than 1, preferably between 1 and 8.

| Typical Properties | Ave. Eq. Wt. | NCO Content, % |
|---|---|---|
| Desmodur N-100 | 191 | 22.0 |
| Desmodur N-3200 | 181 | 23.2 |

The typical NCO content of Desmodur N-100 approximates that listed for a SRI International Report (Isocyanates No. 1D, July, 1983, Page 279) hexamethylene diisocyanate homopolymer with the following composition:

| Product Composition | Wt. % |
|---|---|
| Hexamethylene Diisocyanate | 0.1 |
| Monobiuret | 44.5 |
| Bisbiuret | 17.4 |
| Trisbiuret | 9.5 |
| Tetrabiuret | 5.4 |
| Higher Mol. Wt. Derivatives | 23.1 |
| NCO Content | 21.8 |

Based on its average equivalent weight and NCO content, the comparative bis, tris, tetra, etc., content of Desmodur N-3200 should be less than that of the N-100 product. Desmodur N-3300 is a hexamethylene diisocyanate-derived isocyanurate trimer which can be represented by the formula:

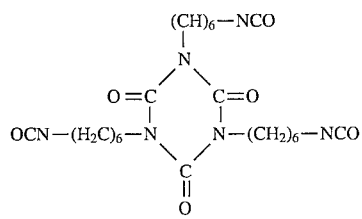

The fluorochemical products of the present invention are typically prepared by first charging to a reaction vessel the polyisocyanate (1), the fluorochemical component (2), the hydrophilic, water-solvatable compound (3), the compound (4) imparting abeyant chemical reactivity to the product of the present invention (provided it does not significantly react with the polyisocyanate in the absence of a catalyst), and a dry, organic solvent such as methylisobutylketone (MIBK). The order of reagent addition is not critical. The specific weight of the polyisocyanate and other reactants charged is based on their equivalent weights and on the working capacity of the reaction vessel and is adjusted so that all Zerevitinov active hydrogens charged will react with some desired value between about 55% and about 95% of the total NCO group charge. The weight of dry solvent is typically 15–30% of the total charge weight. The charge is agitated and temperature adjusted to 40°–70° C. If the reactant imparting abeyant chemical reactivity to the fluorochemical product of the present invention is self-reactive with the polyisocyanate charge, it can be added slowly and with good mixing to the reaction vessel at this point or, alternatively after the catalyzed reaction of the other Zerevitinov active hydrogen containing reactants with the isocyanate charge. A catalyst, typically dibutyltindilaurate per se, or as a solution in an organic solvent, is added to promote the latter reactions in an amount which depends on the charge, but is usually small, e.g. 1 to 2 parts per 10,000 parts of the polyisocyanate. After the resultant exotherm, the mixture is agitated at about 90° C. for 2–20 hours, preferably 2–4 hours from the time of catalyst addition. If the reactant imparting abeyant chemical reactivity to the fluorochemical product has not been added, the reaction mixture is cooled to about 60° C., the reactant is added slowly and with good mixing, and the resultant mixture agitated at 65°–80° C. for an additional 1–2 hours. The reaction mixture is solvent diluted to a solids content of about 70%, treated with sufficient water to react with the residual NCO groups, and agitated at 60°–80° C. for an additional 1–16 hours preferably 2–4 hours. The resultant product can be stored and/or used as prepared or after further solvent dilution. It is preferably converted to and used as a surfactant and organic solvent-free aqueous dispersion.

Suitable substrates for the application of the products of this invention are fibers, yarns, fabrics and other articles made from filaments, fibers or yarns derived from natural, modified natural, or synthetic polymeric materials or from blends of these other fibrous materials and Other porous materials which will absorb and transport low surface tension liquids either on their surfaces on in their interstices by capillary action. Specific representative examples are cotton, silk, regenerated cellulose, nylon, fiber-forming linear polyesters, fiber-forming polyacrylonitrile, cellulose nitrate, cellulose acetate, ethyl cellulose, paper, wood pressed or otherwise hardened wood composites, and the like. Dyed and undyed cotton sateen, poplin, broadcloth, jean cloth, gabardine and the like are especially adaptable for treatment with the compositions of this invention to provide products having oil repellency and soil release properties and which are also relatively unaffected by the action of heat, air and light. Materials treated with the products of this invention retain a high portion of their soil-release properties after laundering and dry cleaning. The novel compounds of this invention impart oil-, and soil-repellency and/or soil-release properties to fibrous and non-fibrous substrates.

Substrates to which it is particularly advantageous to apply the compounds of the present invention so as to impart soil-release properties include those prepared from polyamide fibers (such as nylon), cotton and blends of polyester and cotton, particularly such substrates being used in tablecloths, washable uniforms and the like.

The compounds of the present invention can be applied to suitable substrates by a variety of customary procedures. For application to washable apparel fabrics, the compounds of the present invention can be applied, for example, from an aqueous dispersion or an organic solvent solution by brushing, dipping, spraying, padding, roll-coating, foaming or the like. The compounds of this invention can be applied to the substrate as such or in combination with other textile or fluoro-finishes, processing aids, lubricants, antistains, etc. The compounds can also be blended with other agents which have oil/water repellency and soil release properties and applied to fibers or fabrics. They can be applied to dyed and undyed textile substrates.

The use of a stoichiometric excess of a polyisocyanate assures complete reaction of the fluorinated and nonfluorinated organic compounds; that coupled with subsequent reaction with water provides products of this invention which posses enhanced properties when compared to those of the prior art, particularly when used to treat washable fabrics such as table cloths, uniforms and the like. In addition, those aspects of the invention eliminate any need to remove any unreacted organic compound. It thus provides a substantial process advantage; it also provides greater product purity and uniformity.

TEST METHODS AND PROCEDURES

The following test methods and procedures were used to characterize the products of the present invention.

The Oil Repellency (OR), Soil Release (SR) and wash durability properties of the fluorochemical products were determined after their application to a standard test fabric. The aqueous product dispersions were applied to ca. 8 in.× 25 in. blue 50/50 polyester/cotton knit fabric swatches by padding from an aqueous pad both containing also the following permanent press resin, catalyst, fabric softener and wetting agent:

| | |
|---|---|
| 0.1% Mykon NRW-3 | Sequa Chem. Inc.; wetting agent |
| 10.0% Permafresh 113B | Ciba Geigy; modified DMDHEU resin |
| 2.5% Catalyst 531 | Ciba-Geigy; activated $MgCl_2$ solution |
| 3.0% Ultrasof PFS | Ciba-Geigy; fabric softener |

Percents are percent by weight. Unless otherwise specified, the fluorochemical dispersion was added to the pad both in an amount equivalent to 0.18% fluorine on weight of bath (OWB) and the wet pickup (WPN) of the test fabric adjusted to obtain about 0.11%–0.12% fluorine on weight of fabric (OWF). Fluorine loadings other than 0.11%–0.12% were obtained by appropriate adjustment of the pad bath fluorine content and/or the WPU of the test fabric.

The padded fabric was dried at 300° F. for two minutes and cured at 330° F. for three minutes in a circulating air oven, then cut to obtain three ca. 6 in.× 8 in. swatches plus residual fabric.

Oil repellency rating—repellency of fluorochemical product treated test fabrics to oily liquids was measured using AATCC Test Method 118-1983, "Oil Repellency: Hydrocarbon Resistance Test". According to this test, drops of standard test liquids consisting of a selected series of hydrocarbons with varying surface tension, are placed on the fabric surface. The oil Repellency Rating (ORR) is defined as the highest number test liquid which does not wet the fabric surface. The higher the ORR therefore, the better the repellency of the fabric to oily materials. Wetting of the fabric is normally indicted by a darkening of the fabric at the liquid-fabric interface. The following standard test liquids and rating system are employed:

| ORR | Test Liquid |
|---|---|
| 1 | Nujol |
| 2 | 65/35 Nujol/n-hexadecane (V/V) |
| 3 | n-hexadecane |
| 4 | n-tetradecane |
| 5 | n-dodecane |
| 6 | n-decane |
| 7 | n-octane |
| 8 | n-heptane |

Initial ORR values were measured on the residual (unlaundered) fabric segments.

Soil Release Rating—Soil Release (SR) properties of the fluorochemical products of the present invention were measured using AATCC Test Method 130–1980, "Soil Release: Oily Stain Release Method". According to this test, a stain on a test fabric is produced by using a weight to force a given amount of the staining substance into the fabric. The stained fabric is then laundered in a prescribed manner and the residual stain rated by comparison with a standard stain release replica showing a graduated series of stains. The SR rating can be determined before (initial performance) and/or after consecutive (without intervening dry cycles) laundering of the treated fabric. SR measurements after five or more (i.e., 10, 20, etc.) consecutive wash cycles are typically used to determine the wash durability of the fluorochemical product. The latter can also be monitored by fluorine analysis.

An initial SR performance level was determined by placing the treated, unwashed fabric swatch flat in landscape mode on a single thickness of white blotting paper positioned on a smooth horizontal surface and dropping five drops of a standard dirty motor oil (3M Scotchgard SPS-4003 Test Liquid Stain C) thereon. A sheet of non-absorbant (glassine) paper was placed over the oily puddle and a five pound weight placed thereon for one minute to force the oil into the fabric. The weight and glassine paper were removed, the stained swatch was left at room temperature for one hour, and then washed in a Kenmore heavy duty 70 Series washing machine at cotton/Sturdy heavy cycle and hi water level settings with 120° F. water, four pounds of 50/50 polyester/cotton sheeting ballast and 100 grams Tide detergent. The washed swatch and ballast was tumble dried on high heat for 45 minutes in a Kenmore Heavy Duty Plus electric dryer.

Fluorochemical product treated test fabric which was to be subjected to one or more launderings and a final drying before staining was processed as above, but with 50 grams Tide detergent per prestain wash cycle.

A visual SR rating for the stained, washed fabric swatch was obtained by comparing the residual stain to the eight graduated intensity levels of the 3M Company Stain Release Rating Scale.

| SR Rating | SR Property Observation |
|---|---|
| 1 | Substantial Staining (Poor Cleanability) |
| 8 | Negligible or No Staining (Excellent Cleanability) |

The comparison was made in a Macbeth Spectralight under cool white fluorescent light, with the test fabric placed horizontally on a black surface directly in front of the vertically mounted rating scale. Each stain was assigned an integral rating from 1 to 8, or for intermediate stains, the limiting range, i.e., 4–5.

The unimodal average particle size of the aqueous product dispersions were determined using a Coulter Model N4MD Sub-micron Particle Analyzer with Size Distribution Processor Analysis and Multiple Scattering Angle Detection.

Unless otherwise indicated in the Examples that follow, the fluorinated reactant is the above-described perfluoroalkylethyl alcohol mixture (FA) of the formula: $F(CF_2)_aCH_2CH_2OH$, wherein a is predominantly 6, 8 and 10. In a typical mixture of such fluoroalcohols, the compounds will have the following approximate composition in relation to their $(F(CF_2)_a$ radicals:

0% to 3% wherein a=4,

27% to 37% wherein a=6,

28% to 32% wherein a=8,

14% to 20% wherein a=10,

8% to 13% wherein a=12,

3% to 6% wherein a=14,

0% to 2% wherein a=16,

0% to 1% wherein a=18, and

0% to 1% wherein a=20.

In the Examples that follow, a polyisocyanate containing at least three NCO groups is reacted with a stoichiometric deficiency of a fluorochemical reagent, a hydrophilic water solvatable reagent and a reagent which on reaction with an NCO group yields functionality having abeyant chemical reactivity to obtain an intermediate product mixture with unreacted NCO groups. The subsequent reaction of water with the residual NCO groups is presumed, based on the volume of carbon dioxide liberated to predominantly yield urea group linked products by one or both of the following reaction pathways:

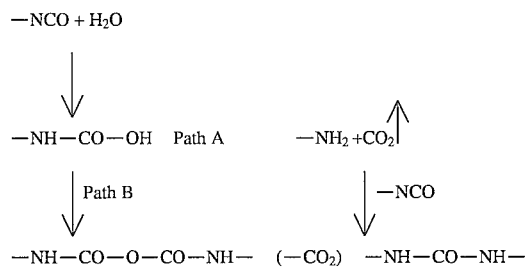

Water reacting by either of the two pathways acts as a dual functional Zerevitinov active hydrogen compound. It is convenient to describe the amount of water added to the synthesis mixture for the second stage reaction sequence in terms of the number of active hydrogen atoms added per number of residual NCO groups, i.e., as a ratio. The theoretical water ratio required to satisfy the stoichiometry of either pathway is at least 1:1.

It is also convenient to describe the urea linkage-containing polyoxyalkylene fluorocarbamates of the present invention as W X Y Z reaction level products, wherein W, X, Y and Z are integers that total 100 and correspond to the percentage reaction of the NCO functionality with the fluorochemical reactant, the hydrophilic, water-solvatable reactant, the reactant imparting abeyant chemical reactivity, and with water or with a water/NCO reaction product, respectively. The most preferred fluorocarbamate of this invention, the reaction product of Example 1, for example, is a 16/24/30/30 reaction level product.

EXAMPLE 1

A hexamethylene diisocyanate (HMDI) homopolymer (Desmodur N- 3200) in dry MIBK solution containing about 13.7% NCO groups, and a perfluoroalkylethyl alcohol mixture (FA) and a 550 average molecular weight methoxypolyethylene glycol mixture (MPEG-550) in amounts sufficient to react with 16% and 24% of the NCO group charge, respectively, were added to a reaction vessel, agitated and heated to about 60° C., whereupon 2-butanone oxime (BO) in an amount sufficient to react with 30% of the NCO group charge was added. After the resultant exotherm, a catalytic amount of dibutyltindilaurate was added and the mixture heated to and held at about 90° C. for two hours from the time of the catalyst addition. The reaction mixture was then MIBK diluted to a solids content of about 70%, treated with water in an amount equal to a water ratio of about four, and agitated at about 75° C. for an additional three hours. Water was then added and the MIBK removed by reduced pressure azeotropic distillation to obtain the 16/24/30/30 reaction level product as a fluid, 41.5% solids—5.1% fluorine content aqueous dispersion with a 390 nanometer unimodal average particle size. There was no change in the physical nature of the product after it was subjected to five successive freeze/thaw cycles, or sheared in an Eberbach semi-micro stainless steel container on a Waring duo-speed blender on high setting for two minutes. The dispersed product was applied to the standard test fabric at four fluorine application levels and cured as described in the Test Methods and Procedures Section. The oil repellency (OR), soil release (SR) and fluorine retention (FR) properties of the treated fabric were measured with the results as shown in Table I.

TABLE 1

| Fluorine | Initial | | SR After Washing | | FR - % After Washing | |
|---|---|---|---|---|---|---|
| ppm OWF | ORR | SR | 5 × | 10 × | 5 × | 10 × |
| 410 | 1 | 4 | 4 | 4 | 63 | 54 |
| 680 | 1 | 7 | 4 | 6 | 56 | 51 |
| 840 | 2 | 7 | 5–6 | 6 | 52 | 40 |
| 1050 | 4 | 7–8 | 5–6 | 6–7 | 50 | 37 |

EXAMPLE 2

A HMDI homopolymer (Desmodur N-3200) in dry MIBK solution containing about 13.5% NCO groups, and a FA mixture and MPEG-750 in amounts sufficient to react with 12.5% and 12.5% of the NCO group change, respectively, were added to a reaction vessel, agitated and heated to about 60° C., whereupon BO in an amount sufficient to react with 70% of the NCO group charge was added. After the resultant exotherm, a catalytic amount of dibutyltindialaurate was added and the mixture heated to and held at about 90° C. for two hours from the time of the catalyst addition. The reaction mixture was then MIBK diluted to a solids content of about 70%, treated with water in an amount equal to a water ratio of about four, and agitated at about 75° C. for an additional two hours. Water was then added and the MIBK removed by reduced pressure azeotropic distillation to recover the 12.5/12.5/70/5 reaction level product as a thick but fluid 46.2% solids content aqueous dispersion.

EXAMPLE 3

A HMDI homopolymer (Desmodur N-3200) in dry MIBK solution containing about 13.6% NCO groups, and a FA mixture and MPEG-750 in amounts sufficient to react with 8% and 12% of the NCO group charge, respectively, were added to a reaction vessel, agitated and heated to about 60° C., whereupon BO in an amount sufficient to react with 60% of the NCO group charge was added. After the resultant exotherm, a catalytic amount of dibutyltindilaurate was added and the mixture heated to and held at about 90° C. for two hours from the time of the catalyst addition. The reaction mixture was then MIBK diluted to a solids content of about 70%, treated with water in an amount equal to a water ratio of about four, and agitated at about 65° C. for an additional hour. Water was then added and the MIBK removed by reduced pressure azeotropic distillation. The 8/12/60/20 reaction level product was recovered as a fluid, 40.0% solids content aqueous dispersion after further dilution with water.

EXAMPLE 4

A 12/8/60/20 reaction level urea linkage-containing methoxypolyoxyethylene fluorocarbamate was prepared using the procedure and reagents of Example 3. The product was recovered as a fluid 45.8% solids content aqueous dispersion.

EXAMPLE 5

A HMDI homopolymer (Desmodur N-3200) in dry MIBK solution containing about 13.7% NCO groups, and a FA mixture and MPEG-750 in amounts sufficient to react with 15% and 15% of the NCO group charge, respectively, were added to a reaction vessel, agitated and heated to about 50° C., whereupon BO in an amount sufficient to react with 60% of the NCO group charge was added. After the resultant exotherm, a catalytic amount of dibutyltindilaurate was added and the mixture heated to and held at about 90° C. for two hours from the time of the catalyst addition. The reaction mixture was then MIBK diluted to a solids content of about 70%, treated with water in an amount equal to a water ratio of about four, and agitated at about 75° C. for an additional two hours. Water was then added and the MIBK removed by reduced pressure azeotropic distillation. The 15/15/60/10 reaction level product was recovered as a fluid, 39.6% solids content aqueous dispersion after further dilution with water.

EXAMPLE 6

A 12/18/50/20 reaction level urea linkage-containing methoxypolyoxyethylene fluorocarbamate was prepared using the procedure and reagents of Example 5, except the BO was added at an initial temperature of about 60° C. The product was recovered as a fluid, 40.1% solids content aqueous dispersion after further dilution with water.

EXAMPLE 7

A 12/18/50/20 reaction level urea linkage-containing methoxypolyoxyethylene fluorocabamate was prepared using the procedure and reagents of Example 3, except the water treatment reaction time was about 1½ hours. The product was recovered as a fluid 40.3% solids content aqueous dispersion after further dilution with water.

EXAMPLE 8

The product of Example 7 was stored at 50° C. for fourteen days.

EXAMPLE 9

A 24/16/40/20 reaction level urea linkage-containing methoxypolyoxyethylene fluorocarbamate was prepared using the procedure and reagents of Example 3. The product was recovered as a fluid, 43.0% solids content aqueous dispersion.

Control A

A HMDI homopolymer (Desmodur N-3200) in dry MIBK solution containing about 13.7% NOD groups, and a FA mixture and MPEG-750 in amounts sufficient to react with 40% and 20% of the NCO group charge, respectively, were added to a reaction vessel, agitated and heated to about 60° C., whereupon a catalytic amount of dibutyltindilaurate was added. After the resultant exotherm, the reaction mixture was heated to and held at about 90° C. for three hours from the time of the catalyst addition. The reaction mixture was then MIBK diluted to a solids content of about 65%, treated with water in an amount equal to a water ratio of about two, and agitated at about 75° C. for an additional three hours. Water was then added and the MIKB removed by reduced pressure azeotropic distillation to recover the 40/20/0/40 reaction level product as a fluid, 38.3% solids content aqueous dispersion with a 266 nanometer unimodal average particle size.

The dispersed products of Examples 2–9 and Control A were applied to the standard test fabric and cured as described in the Test Methods and Procedures Section. The OR, SR and FR properties of the treated fabric were measured with the results as shown in Table 2.

TABLE 2

| Example Number | Reaction Level | Product % Solids | Product % Fluorine | Initial OR | SR After Washing 5× | SR After Washing 10× | FR - % After Washing 5× | FR - % After Washing 10× |
|---|---|---|---|---|---|---|---|---|
| 2 | 12.5/12.5/75/5 | 46.2 | 4.7 | 4 | 3–4 | 4 | 76 | 70 |
| 3 | 8/12/60/20 | 40.0 | 2.9 | 2 | 7 | 7–8 | 74 | 69 |
| 4 | 12/8/60/20 | 45.8 | 5.1 | 3 | 6 | 6 | 78 | 72 |

TABLE 2-continued

| Example Number | Reaction Level | Product % Solids | Product % Fluorine | Initial OR | SR After Washing 5× | SR After Washing 10× | FR - % After Washing 5× | FR - % After Washing 10× |
|---|---|---|---|---|---|---|---|---|
| 5 | 15/15/60/10 | 39.6 | 4.6 | 5 | 5–6 | 5 | 62 | 55 |
| 6 | 12/18/50/20 | 40.1 | 3.7 | 4 | 7 | 7–8 | 61 | 51 |
| 7 | 12/18/50/20 | 40.3 | 3.8 | 3 | 6 | 6–7 | 58 | 54 |
| 8 | 12/18/50/20 | 40.3 | 3.8 | 3 | 6–7 | 6 | 79 | 70 |
| 9 | 24/16/40/20 | 43.0 | 7.4 | 4 | 6–7 | 6 | 52 | 46 |
| Control A | 40/20/0/40 | 38.3 | 9.3 | 4 | 2 | 2 | 25 | 21 |

EXAMPLES 10–20

A series of urea linkage-containing methoxypolyoxyethylene fluorocarbamates were prepared using the procedure and reagents of Example 1 but at varying reaction levels as identified in Table 3. The product dispersions were applied to the standard test fabric and cured as described in the Test Methods and Procedures Section.

TABLE 3

| Example Number | Reaction Level | Product % Solids | Product % Fluorine | Initial OR | SR After Washing 5× | SR After Washing 10× |
|---|---|---|---|---|---|---|
| 10 | 7/28/35/30 | 43.3 | 2.5 | 3 | 7 | 6–7 |
| 11 | 10/30/35/25 | 39.2 | 3.0 | 4 | 7 | 7 |
| 12 | 10/30/20/40 | 43.3 | 3.4 | 4 | 7 | 7 |
| 13 | 18.3/36.7/15/30 | 42.8 | 5.3 | 5 | 5–6 | 5–6 |
| 14 | 13.3/26.7/15/45 | 37.9 | 4.0 | 3 | 6 | 6 |
| 15 | 20/30/30/20 | 46.4 | 6.4 | 4 | 6 | 5 |
| 16 | 16/24/15/45 | 39.2 | 5.0 | 4 | 6–7 | 5–6 |
| 17 | 15/15/60/10 | 41.6 | 5.2 | 4 | 6 | 6 |
| 18 | 15/15/30/40 | 30.2 | 4.0 | 4 | 6 | 7 |
| 19 | 18/12/40/30 | 37.3 | 5.9 | 4 | 6 | 5 |
| 20 | 23.5/11.5/35/30 | 36.0 | 7.0 | 4 | 5–6 | 4 |
| Control B | Commercial Soil Release FC-248 of 3M Co. | | | 4 to 5 | 1–2 to 3–4* | 1 to 3* |

*Over 16 tests, FC-248 treated fabrics varied within the limits shown.

Control C

A 16/24/30/30 reaction level alkoxypolyoxyalkylene fluorocarbamate was prepared using the procedure and reagents of Example 1, except that a 740 average molecular weight butoxypolyoxypropylene mixture (UCON LB-165, Union Carbide Corporation) was substituted for the MPEG-550 of Example 1. The reaction product was recovered as a taffy-like mass which was not self dispersible in water.

Control D

A 16/24/30/30 reaction level polyoxyethylene fluorocarbamate was prepared using the procedure and reagents of Example 1, except that a 600 average molecular weight polyethylene glycol mixture (PEG-600) was substituted for the MPEG-550 of Example 1. The reaction product was recovered as a soft, particulate mass which was not dispersible in water.

Control E

A 16/24/30/30 reaction level polyoxyethylene fluorocarbamate was prepared using the procedure and reagents of Example 1, except that polyoxyethylene (20) sorbitan monolaurate (Tween 20, ICI Americas, Inc.) was substituted for the MPEG-550 of Example 1. The reaction product was recovered as a soft particulate mass which was not dispersible in water.

EXAMPLE 21

A 14/21/60/5 reaction level urea linkage-containing methoxypolyoxyethylene fluorocarbamate was prepared using the procedure and reagents of Example 3, except that MPEG-350 was substituted for the MPEG-750 of Example 3 and the water ratio was 1.6.

EXAMPLE 22

A 15/30/50/5 reaction level urea linkage-containing methoxypolyoxyethylene fluorocarbamate was prepared using the procedure and reagents of Example 21, except that the water ratio was 2.1.

EXAMPLE 23

A HMDI homopolymer (Desmodur N-3200) in dry MIBK solution containing about 13.6% NCO groups, and a FA mixture, MPEG-350 and MPEG-550 in amounts sufficient to react with 12%, 9% and 9% of the NCO group charge, respectively, were added to a reaction vessel, agitated and heated to about 60° C., whereupon BO in an amount sufficient to react with 50% of the NCO group charge was added. After the resultant exotherm, a catalytic amount of dibutyltindilaurate was added, and the mixture heated to and held at about 90° C. for two hours from the time of the catalyst addition. The reaction mixture was then MIBK diluted to a solids content of about 70%, treated with water in an amount equal to a water ratio of four, and agitated at about 75° C. for an additional two hours. Water was then added and the MIBK removed by reduced pressure azeotropic distillation. The 12/9,9/50/20 reaction level product was recovered as a fluid, 40.3% solids content aqueous dispersion after further dilution with water.

EXAMPLE 24

A HMDI homopolymer (Desmodur N-3200) in dry MIBK solution containing about 13.6% NCO groups, and a FA mixture, MPEG-350 and MPEG- 750 in amounts sufficient to react with 10%, 10% and 10% of the NCO group charge, respectively, were added to a reaction vessel, agitated and heated to about 60° C., whereupon BO in an amount sufficient to react with 60% of the NCO group charge was added. After the resultant exotherm, a catalytic amount of dibutyltindilaurate was added, and the mixture heated to and held at about 90° C. for two hours from the time of the catalyst addition. The reaction mixture was then MIBK diluted to a solids content of about 70%, treated with water in an amount equal to a water ratio of 3.7, and agitated at about 65° C. for an additional hour. Water was then added and the MIBK removed by reduced pressure azeotropic distillation. The 10/10,10/60/10 reaction level product was recovered as a fluid, 39.9% solids content aqueous dispersion after further dilution with water.

The dispersed products of Examples 21–24 were applied to the standard test fabric and cured as described in the Test Methods and Procedures Section. The OR and SR properties of the treated fabric were measured with the results as shown in Table 4.

TABLE 4

| Example Number | Reaction Level | Product % Solids | Product % Fluorine | Initial OR | SR After Washing 5× | SR After Washing 10× |
|---|---|---|---|---|---|---|
| 21 | 14/21/60/5 | 34.8 | 4.2 | 5 | 6–7 | 6–7 |
| 22 | 15/30/50/5 | 39.9 | 4.8 | 5 | 5 | 6 |
| 23 | 12/9,9/50/20 | 40.3 | 4.3 | 4 | 6 | 6 |
| 24 | 10/10,10/60/10 | 39.9 | 3.1 | 4 | 6 | 6 |

EXAMPLES 25–30

A series of 20/20/30/30 reaction level urea linkage-containing alkoxypolyoxyethylene fluorocarbamates were prepared using the procedure and reagents of Example 1, except that alkoxypolyoxyethylene mixtures with the average molecular weight and the hydrocarbon substituent (HCS) indicated in Table 5 were substituted for the MPEG-550 of Example 1.

TABLE 5

| Example Number | Alkoxypolyoxyethylene HCS | MW | EO's | Product Dispersion Solids, % | Fluorine, % | Particle Size, nm |
|---|---|---|---|---|---|---|
| 25 | methyl | 450 | 9.5 | 31.8 | 5.2 | |
| 26 | methyl | 950 | 20.9 | 39.6 | 5.2 | 244 |
| 27 | methyl | 2000 | 44.7 | 35.0 | 3.3 | 528 |
| 28 | allyl | 750 | 15.7 | 43.3 | 6.0 | |
| 29 | n-pentyl | 1067 | 22.3 | 36.2 | 4.4 | |
| 30 | cyclohexyl | 765 | 15.1 | 36.7 | 5.2 | |

EXAMPLES 31 and 32

A series of 20/20/30/30 reaction level urea linkage-containing alkoxypolyoxyalkylene fluorocarbamates were prepared using the procedure and reagents of Example 1, except that butoxypolyoxyalkylene mixtures (UCON HB-50 Fluids, Union Carbide Corporation) containing equal amounts by weight of oxyethylene (EO) and oxypropylene (PO), as indicated in Table 6, were substituted for the MPEG-550 of Example 1.

TABLE 6

| Example Number | UCON Fluid Designation | MW. Ave. | Product Dispersion Solids, % | Fluorine, % |
|---|---|---|---|---|
| 31 | 50-HB-400 | 1230 | 37.3 | 4.3 |
| 32 | 50-HB-660 | 1590 | 38.8 | 4.0 |

EXAMPLE 33

A HMDI homopolymer (Desmodur N-3200) in dry MIBK solution containing about 13.2% NCO groups, and a FA mixture and MPEG-750 in amounts sufficient to react with 15% and 15% of the NCO group charge, respectively, were added to a reaction vessel, agitated and heated to about 60° C., whereupon a catalytic amount of dibutyltindilaurate was added. After the resultant exotherm, the reaction mixture was heated to and held at about 90° C. for two hours from the time of the catalyst addition, and then cooled to about 55° C. After BO in an amount sufficient to react with 60% of the NCO group charge was added, the reaction mixture was agitated for one hour at about 65° C., then MIBK diluted to a solids content of about 70%, treated with water in an amount equal to a water ratio of about four, and agitated at about 65° C. for an additional hour. Water was then added and the MIBK removed by reduced pressure azeotropic distillation. The 15/15/60/10 reaction level product was recovered as a fluid, 39.5% aqueous dispersion after further dilution with water.

EXAMPLE 34

A HMDI homopolymer (Desmodur N-3200) in dry MIBK solution containing about 13.6% NCO groups, and a perfluoroalkylethyl alcohol mixture (FA), MPEG-750 and glycidol in amounts sufficient to react with 18.75%, 18.75% and 55% of the NCO group charge, respectively, were added to a reaction vessel, agitated and heated to 53° C., whereupon a catalytic amount of dibutyltindilaurate was added. After the resultant exotherm, the reaction mixture was heated to and held at about 90° C. for two hours from the time of the catalyst addition. The reaction mixture was then MIBK diluted to a solids content of about 70%, treated with water in an amount equal to a water ratio of about two, and agitated at about 65° C. for an additional hour. Water was then added and the mixture MIBK stripped by reduced pressure azeotropic distillation to recover the 18.75/18.75/55/7.5 reaction level product as a fluid, 36.5% solids content aqueous dispersion.

EXAMPLE 35

A HMDI homopolymer (Desmodur N-3200) in dry MIBK solution containing about 13.6% NCO groups, and a perfluoroalkylethyl alcohol mixture (FA), MPEG-550 and glycidol in amounts sufficient to react with 16%, 24% and of the NCO group charge, respectively, were added to reaction vessel, agitated and heated to about 60° C., whereupon a catalytic amount of dibutlyltindilaurate was added. After the resultant exotherm, the reaction mixture was heated to and held at about 90° C. for two hours from the time of the catalyst addition. The reaction mixture was then MIBK diluted to a solids content of about 70%, treated with water in an amount equal to a water ratio of about four, and agitated at about 75° C. for an additional three hours. Water was then added and the mixture MIBK stripped by reduced pressure azeotropic distillation to recover the 16/24/20/40 reaction level product as a thick, 50.6% solids content aqueous dispersion which was subsequently water diluted to 31.9% solids.

EXAMPLE 36

The procedure and reagents of Example 35 were used to prepare a 13.3/26.7/20/40 reaction level product which, initially recovered as a fluid, 41.1% solids content aqueous dispersion, was subsequently water diluted to a 4.0% fluorine, 37.9% solids content product.

The dispersed products of Examples 34–36 were applied at a target 1200 ppm fluorine OWF level by padding and cured as described in the Test Methods and Procedures Section. The SR properties of the treated fabrics were measured, with the results as shown in Table 7.

TABLE 7

| Example Number | Reaction Level | Dispersed Product, % Solids | Dispersed Product, % Fluorine | SR After Washing 5× | SR After Washing 10× |
|---|---|---|---|---|---|
| 34 | 18.75/18.75/55/7.5 | 36.5 | 4.9 | 4–5 | 4 |
| 35 | 16/24/20/40 | 31.9 | 4.1 | 6 | 5–6 |
| 36 | 13.3/26.7/20/40 | 37.9 | 4.0 | 6 | 6–7 |

EXAMPLE 37

A HMDI homopolymer (Desmodur N-100) in dry MIBK solution containing about 12.6% NCO groups and a FNA mixture and MPEG-750 in amounts sufficient to react with 16% and 24% of the NCO group charge, respectively, were added to a reaction vessel, agitated and heated to about 60° C., whereupon acetone oxime in an amount sufficient to react with 30% of the NCO group charge was added. After the resultant exotherm, a catalytic amount of dibutlyltindilaurate was added and the mixture heated to and held at about 90° C. for two hours from the time of the catalyst addition. The reaction mixture was then MIBK diluted to a solids content of about 70%, treated with water in an amount equal to a water ratio of about four, and agitated at about 75° C. for three additional hours. Water was then added and the MIBK removed by reduced pressure azeotropic distillation. The 16/24/30/30 reaction level product was recovered as a fluid, 37.8% solids—4.5% fluorine content aqueous dispersion after further dilution with water.

EXAMPLE 38

A 16/24/30/30 reaction level urea linkage-containing methoxypolyoxyethylene fluorocarbamate was prepared using the procedure and reagents of Example 1, except that cyclohexanone oxime was substituted for the BO of Example 1. The product was recovered as a fluid, 43.1% solids—5.3% fluorine content aqueous dispersion.

EXAMPLE 39

A 16/24/30/30 reaction level urea linkage-containing methoxypolyoxyethylene fluorocarbonate was prepared using the procedure and reagents of Example 1, except that N-methyl-N-ethanolperfluorooctanesulfonamide was substituted for the FA mixture of Example 1. The product was recovered as a fluid, 32.9% solids—3.9% fluorine content aqueous dispersion after further dilution with water.

EXAMPLE 40

A 16/24/30/30 reaction level urea linkage-containing methoxypolyoxethylene fluorocarbamate was prepared using the procedure and reagents of Example 1, except that N-propyl-N-ethanolperfluorooctanesulfonamide was substituted for the FA mixture of Example 1. The product was recovered as a fluid 40.1% solids—4.7% fluorine content aqueous dispersion after further dilution with water.

EXAMPLE 41

A HMDI homopolymer (Desmodur N-3200) in dry MIBK solution containing about 13.7% NCO groups, and a perfluoroalkylethylthiol mixture (PFT)* and MPEG-550 in amounts sufficient to react with 16% and 24% of the NCO group charge, respectively, were added to a reaction vessel, agitated and heated to about 60° C., whereupon BO in an amount sufficient to react with 30% of the NCO group charge was added. After the resultant exotherm, a catalytic amount of dibutyltindilaurate was added and the mixture heated to and held at about 90° C. for 23 hours from the time of the catalyst addition. The reaction mixture was then MIBK diluted to a solids content of about 70%, treated with water in an amount equal to a water ratio of about four, and agitated at about 75° C. for about 4½ hours. Water was then added and the MIBK removed by reduced pressure azeotropic distillation. The 16/24/30/30 reaction level product was recovered as a fluid, 40.1% solids—5.3% fluorine content aqueous dispersion after further dilution with water.

A perfluoroalkylethylthiol mixture of the formula: $F(CF_2)_a CH_2 CH_2 SH$ wherein a is predominantly 8 and 10; in a typical mixture of which the fluorothiols will have the same approximate composition in relation to their $F(CF_2)_a$ radicals as cited for the FNA mixture.

EXAMPLE 42

A 16/24/30/30 reaction level urea linkage-containing methoxypolyoxyethylene fluorocarbamate was prepared using the procedure and reagents of Example 1, except that MPEG-750 and a perfluoroalkylpropylamine mixture* were substituted for the MPEG-550 and FA mixture of Example 1. The product was recovered as a fluid 45.7% solids—5.4% fluorine content aqueous dispersion.

A perfluoroalkylpropylamine mixture of the formula $F(CF_2)_a CH_2 CH_2 CH_2 —NH_2$ wherein a is predominantly 8, 10 and 12 in a typical mixture of which the fluoroamines will have the following approximate composition in relation to their $F(CF)_2$ radicals:

0% to 3% wherein a=6,
45% to 52% wherein a=8,
26% to 32% wherein a=10,
8% to 14% wherein a=12, and
1% to 5% wherein a=14

EXAMPLE 43

A 24/16/30/30 reaction level urea linkage-containing methoxypolyoxyethylene fluorocarbamate was prepared using the procedure and reagents of Example 1, except that 2,2,2,3,3,3-hexafluoroisopropanol was substituted for the FA mixture of Example 1. The product was recovered as a fluid, 36.7% solids—2.9% fluorine content aqueous dispersion.

EXAMPLE 44

A 16/24/30/30 reaction level urea linkage-containing methoxypolyoxyethylene fluorocarbamate was prepared using the procedure and reagents of Example 1, except that 1,1-dihydroperfluorohexanol was substituted for the FA mixture of Example 1. The product was recovered as a fluid, 42.8% solids—3.6% fluorine content aqueous dispersion.

EXAMPLE 45

A 16/24/30/30 reaction level urea linkage-containing methoxypolyoxyethylene fluorocarbamate was prepared using the procedure and reagents of Example 1, except that a N-perfluoroalkylethyl-N-phenylamine mixture* was substituted for the FA mixture of Example 1. The product was recovered as a fluid, 38.8% solids—3.8% fluorine content aqueous dispersion.

A N-perfluoroalkylethyl-N-phenylamine mixture of the formula: $F(CF_2)_aCH_2CH_2-NH-C_6H_5$ wherein a is predonimantly 6 and 8; in a typical mixture of which the amines will have the following approximate composition in relation to their $F(CF_2)_a$ radicals:
5% to 7% wherein a=4
46% to 53% wherein a=6
25% to 29% wherein a=8
5% to 11% wherein a=10
1% to 4% wherein a=12

EXAMPLE 46

A 16/24/30/30 reaction level urea linkage-containing methoxypolyoxyethylene fluorocarbamate was prepared using the procedure and reagents of Example 1, except that a ca 60/40 mixture of diperfluorooctylethyl amine and N-perfluorooctylethyl-N-3,4,4,5,5,6,6,7,7,8,8,9,9,10,10-hexadecafluoro-2-decene-1-amine was substituted for the FA mixture of Example 1. The product was recovered as a fluid, 46.2% solids—8.5% fluorine content aqueous dispersion.

EXAMPLE 47

A 16/24/15/45 reaction level urea linkage-containing methoxypolyoxyethylene fluorocarbamate was prepared using the procedure and reagents of Example 1, except that a HMDI derived isocyanurate trimer (Desmodur N-3300) was substituted for the HMDI homopolymer of Example 1.

EXAMPLE 48

A 13.3/26.7/25/35 reaction level urea linkage-containing methoxypolyoxyethylene fluorocarbamate was prepared using the procedure and reagents of Example 1, except that a 3-isocyanatomethyl-3,5,5-trimethylcyclohexyl isocyanate derived isocyanurate trimer (IPDI adduct T1890/100, Huls) was substituted for the HMDI homopolymer of Example 1.

EXAMPLE 49

A 13.3/26.7/25/35 reaction level urea linkage-containing methoxypolyoxyethylene fluorocarbamate was prepared using the procedure and reagents of Example 1, except that a trifunctional polyisocyanate derived from toluene diisocyanate and 1,1,1-tris(hydroxymethyl)propane (Mondur CB-75) was substituted for the HMDI homopolymer of Example 1.

EXAMPLE 50

A 13.3/26.7/20/40 reaction level urea linkage-containing methoxypolyoxyethylene fluorocarbamate was prepared using the procedure and reagents of Example 1, except that a trifuntional polyisocyanate derived from m-tetramethylxylene diisocyanate and 1,1,1-tris(hydroxymethyl)propane (Cythane 2601) was substituted for the HMDI homopolymer of Example 1.

The dispersed products of Examples 47–50 were applied to the standard test fabric and cured as described in the Test Methods and Procedures Section. The SR properties of the treated fabric were measured with the results as shown in Table 8.

TABLE 8

| Example Number | Reaction Level | Product, % Solids | Product, % Fluorine | SR After Washing 5× | SR After Washing 10× |
| --- | --- | --- | --- | --- | --- |
| 47 | 16/24/15/45 | 32.2 | 4.0 | 6 | 6 |
| 48 | 13.3/26.7/25/35 | 23.1 | 2.1 | 6 | 4–5 |
| 49 | 13.3/26.7/25/35 | 40.3 | 3.6 | 5–6 | 4–5 |
| 50 | 13.3/26.7/20/40 | 18.9 | 1.5 | 6–7 | 6 |

EXAMPLE 51

A 16/24/30/30 reaction level urea linkage-containing methoxypolyoxyethylene fluorocarbamate was prepared using the procedure and reagents of Example 1, except that 50% of the total NCO group charge was supplied by a HMDI derived isocyanurate (Desmodur N-3300). The product was recovered as a fluid, 40.0% solids content aqueous dispersion after further dilution with water.

I claim:

1. A self-emulsifiable aqueous soil-release composition comprising urea linkage-containing alkoxy polyoxtalkylene fluorocarbamates prepared by reacting (a) at least one polyisocyanate which contains at least three isocyanate groups per molecule with (b) at least one fluorochemical reagent whcih contains per molecule a single functional; group which has at least one reactive Zerewitinoff hydrogen atom and at least two carbon atoms each of which contains at least two fluorine atoms, said fluorochemical reagent reacting with about 7% to about 24% of said isocyanate groups, (c) at least one hydrophilic reagent able to be solvated by water which contains per molecule a single functional group which has at least one reactive Zerewitinoff hydrogen atom, and said hydrophilic reagent reacting with about 8% to about 37% of said isocyanate groups, and (d) at least one reagent which contains at least one reactive Zerewitinoff hydrogen atom and which on reaction with an isocyanate group yields functionality which has abeyant chemical reactivity with fibrous substrates which contain reactive Zerewitinoff hydrogen atoms, said reagent which yields said abeyant chemical reactivity reacting with about 15% to about 60% of said isocyanate groups, and then with (e) water, the equivalent weights of said polyisocyanate and said reagents (b), (c) and (d) being such that said reagents will react with 55% to 95% of said isocyanate groups, and water will react with all of the remaining isocyanate groups.

2. The composition of claim 1 wherein said fluorochemical reagent is a perfluoroalkylethyl alcohol mixture of the formula $F(CF_2)_aCH_2CH_2OH$, wherein a is predominantly 6,8 and 10.

3. The composition of claim 1 wherein said fluorochemical reagent is a perfluoroalkylethyl alcohol mixture of the formula $F(CF_2)_aCH_2CH_2OH$, wherein a is predominantly 8, 10 and 12.

4. The products composition of claim 1 wherein said hydrophilic reagent is at least one ethylene oxide (EO) or ethylene oxide/propylene oxide (PO) derived polymer of the general formula

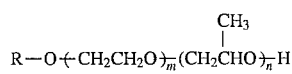

wherein

R is a monovalent hydrocarbon radical containing no more than six aliphatic or alicyclic carbon atoms, and m and n are the average number of repeating oxyethylene groups, respectively; provided that m is always a positive integer, while n is a positive integer or zero, and m and n are such that the average molecular weight of component (c) is a maximum of about 2000.

5. The product composition of claim 4 wherein n is zero.

6. The composition of claim 5 wherein R is methyl.

7. The compositions of claim 1 wherein said reagent (d) is an isocyanate-blocking agent or an epoxyalcohol.

8. The composition of any of claims 1 through 5 wherein said isocyanate is represented by the formula

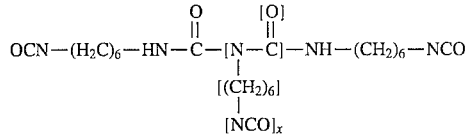

wherein x is an integer equal to or greater than 1.

9. The composition of claim 8 wherein x is an integer between 1 and 8.

* * * * *